US008821382B2

(12) United States Patent
Kagawa

(10) Patent No.: US 8,821,382 B2
(45) Date of Patent: Sep. 2, 2014

(54) IMAGE PICKUP UNIT

(75) Inventor: Hiroaki Kagawa, Sagamihara (JP)

(73) Assignee: Olympus Medical Systems Corp., Tokyo (JP)

(*) Notice: Subject to any disclaimer, the term of this patent is extended or adjusted under 35 U.S.C. 154(b) by 100 days.

(21) Appl. No.: 13/154,831

(22) Filed: Jun. 7, 2011

(65) Prior Publication Data

US 2011/0295064 A1 Dec. 1, 2011

Related U.S. Application Data

(63) Continuation of application No. PCT/JP2010/060674, filed on Jun. 23, 2010.

(30) Foreign Application Priority Data

Jun. 25, 2009 (JP) ................................ 2009-151300

(51) Int. Cl.
*A61B 1/04* (2006.01)
*A61B 1/06* (2006.01)
*A61B 1/05* (2006.01)

(52) U.S. Cl.
CPC .. *A61B 1/04* (2013.01); *A61B 1/051* (2013.01)
USPC .............. 600/110; 600/160; 600/109; 348/76

(58) Field of Classification Search
CPC .......... A61B 1/05; A61B 1/018; A61B 1/041; A61B 1/042; H04N 2005/2255; H01R 31/06
USPC ......... 600/110, 104, 112, 130, 118, 160, 101, 600/459, 109; 348/76, 374, 65, 294; 439/578; 361/749, 748
See application file for complete search history.

(56) References Cited

U.S. PATENT DOCUMENTS 4,831,456 A * 5/1989 Takamura ..................... 348/374
5,010,446 A * 4/1991 Scannell ....................... 361/749

(Continued)

FOREIGN PATENT DOCUMENTS

JP 05-211997 8/1993
JP 09-069983 3/1997

(Continued)

OTHER PUBLICATIONS

International Search Report dated Aug. 10, 2010.

(Continued)

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

An image pickup unit includes a board to which an image pickup device is electrically connected, the board is provided with a first terminal portion which includes a plurality of terminals and is used when a first endoscope is configured, and a second terminal portion which includes a plurality of terminals and is used when a second endoscope is configured, a folding portion is provided between the first terminal portion and the second terminal portion of the board, when the board is used as an image pickup unit of the second endoscope, the board is folded at the folding portion, and a signal transmission member is connected to the second terminal portion, and at least one of a terminal size and a space between terminals in the second terminal portion is set to be larger than at least one of a terminal size and a terminal space in the first terminal portion.

7 Claims, 10 Drawing Sheets

(56) References Cited

U.S. PATENT DOCUMENTS

| | | | | |
|---|---|---|---|---|
| 5,021,888 | A * | 6/1991 | Kondou et al. | 348/76 |
| 5,220,198 | A * | 6/1993 | Tsuji | 257/731 |
| 5,411,020 | A * | 5/1995 | Ito | 600/146 |
| 5,454,366 | A * | 10/1995 | Ito et al. | 600/109 |
| 5,754,313 | A * | 5/1998 | Pelchy et al. | 358/473 |
| 6,142,930 | A * | 11/2000 | Ito et al. | 600/109 |
| 6,313,456 | B1 * | 11/2001 | Miyashita et al. | 250/208.1 |
| 6,417,885 | B1 * | 7/2002 | Suzuki et al. | 348/374 |
| 7,773,122 | B2 * | 8/2010 | Irion et al. | 348/222.1 |
| 7,775,971 | B2 * | 8/2010 | Fujimori et al. | 600/110 |
| 7,801,586 | B2 * | 9/2010 | Muratayev et al. | 600/407 |
| 7,868,429 | B2 * | 1/2011 | Chen et al. | 257/668 |
| 7,998,065 | B2 * | 8/2011 | Avni | 600/130 |
| 8,137,265 | B2 * | 3/2012 | Joko et al. | 600/118 |
| 8,189,062 | B2 * | 5/2012 | Irion et al. | 348/222.1 |
| 8,289,720 | B2 * | 10/2012 | Ishikawa | 361/749 |
| 2002/0080233 | A1 * | 6/2002 | Irion et al. | 348/65 |
| 2004/0075620 | A1 * | 4/2004 | Tanaka et al. | 345/1.1 |
| 2004/0171914 | A1 * | 9/2004 | Avni | 600/160 |
| 2005/0007130 | A1 * | 1/2005 | Yoshida et al. | 324/754 |
| 2005/0143658 | A1 * | 6/2005 | Saiga | 600/462 |
| 2005/0143659 | A1 * | 6/2005 | Saiga | 600/463 |
| 2006/0001820 | A1 * | 1/2006 | Cheng et al. | 349/150 |
| 2006/0087022 | A1 * | 4/2006 | Chao et al. | 257/688 |
| 2006/0157271 | A1 * | 7/2006 | Miura et al. | 174/250 |
| 2006/0241422 | A1 * | 10/2006 | Muratayev et al. | 600/435 |
| 2007/0081309 | A1 * | 4/2007 | Urushibara et al. | 361/748 |
| 2007/0096234 | A1 * | 5/2007 | Tanaka et al. | 257/433 |
| 2007/0229656 | A1 * | 10/2007 | Khait et al. | 348/77 |
| 2008/0131112 | A1 * | 6/2008 | Aoki et al. | 396/429 |
| 2009/0027491 | A1 * | 1/2009 | Irion et al. | 348/65 |
| 2009/0082624 | A1 * | 3/2009 | Joko et al. | 600/109 |
| 2009/0126976 | A1 * | 5/2009 | Iida | 174/254 |
| 2009/0227147 | A1 * | 9/2009 | Momose | 439/638 |
| 2009/0259101 | A1 * | 10/2009 | Unsai | 600/110 |
| 2009/0268019 | A1 | 10/2009 | Ishii et al. | |
| 2009/0283300 | A1 * | 11/2009 | Grunthaner | 174/254 |
| 2009/0292169 | A1 * | 11/2009 | Mitani et al. | 600/110 |
| 2010/0016039 | A1 * | 1/2010 | Tokuyama | 455/575.3 |

FOREIGN PATENT DOCUMENTS

| | | |
|---|---|---|
| JP | 09-192091 | 7/1997 |
| JP | 09-201331 | 8/1997 |
| JP | 09-307087 | 11/1997 |
| JP | 10-216084 | 8/1998 |
| JP | 11-076156 | 3/1999 |
| JP | 2001-095758 | 4/2001 |
| JP | 2001-104247 | 4/2001 |
| JP | 2001-120501 | 5/2001 |
| JP | 2008-177701 | 7/2008 |
| JP | 2008-227733 | 9/2008 |
| WO | WO 0072744 A2 * | 12/2000 |
| WO | WO 2008/087771 A1 | 7/2008 |

OTHER PUBLICATIONS

Extended Supplementary European Search Report dated Dec. 5, 2012 from related application EP 10792143.9-1265.

* cited by examiner

IMAGE PICKUP UNIT

CROSS REFERENCE TO RELATED APPLICATION

This application is a continuation application of PCT/JP2010/060674 filed on Jun. 23, 2010 and claims benefit of Japanese Application No. 2009-151300 filed in Japan on Jun. 25, 2009, the entire contents of which are incorporated herein by this reference.

BACKGROUND OF THE INVENTION

1. Field of the Invention

The present invention relates to an image pickup unit which is contained in an insertion portion distal end portion of an endoscope including an insertion portion which can be introduced into a subject.

2. Description of the Related Art

In recent years, endoscopes have been used in various medical fields such as internal medicine, surgery or the like. In a surgical operation, in order to decrease invasion to a patient, a laparoscopic surgical operation of performing curative treatment without performing abdominal section is performed. In a laparoscopic surgical operation, a trocar which guides an endoscope for observation into a body cavity, and a trocar which guides a treatment instrument to a site to be treated in the body cavity are punctured into an abdomen of a patient. As the endoscope for observation, a so-called rigid endoscope (hereinafter, also simply described as a rigid scope) is used, in which a bending portion is not present in the vicinity of a distal end of an insertion portion and the insertion portion is formed of a rigid member.

Further, in recent years, for example, a rigid scope with a bending portion which includes the bending portion in the vicinity of a distal end portion has been used as a rigid scope.

Meanwhile, an endoscope (hereinafter, also described as a flexible endoscope) is used, which enables observation by insertion of an insertion portion elongated and having flexibility into a body from natural openings such as a mouth and an anus, or various remedies or treatments by insertion of a treatment instrument into a treatment instrument channel provided in an insertion portion in accordance with necessity. Generally in a flexible endoscope, a bending portion is included in the vicinity of a distal end portion, and the above described bending portion can be bent in response to an operation of a user.

Rigid endoscopes and flexible endoscopes include optical endoscopes and electronic endoscopes. In an optical endoscope, an optical image observed through an observation window is transmitted to an eyepiece portion by an image guide configured by an optical fiber bundle inserted into an insertion portion or a relay lens, and, for example, a surgeon can visually perform observation by peeping into the eyepiece portion.

Meanwhile, in an electronic endoscope, an optical image observed through an observation window is formed on an image pickup surface of an image pickup device such as a CCD which is placed at a distal end portion of an insertion portion. The optical image which is formed on the image pickup surface is converted into an electric signal in the image pickup device, and thereafter, is transmitted to a video processor and is converted into a video signal. Subsequently, the video signal is outputted to a display apparatus, whereby an endoscopic image is displayed on a screen and can be observed. In the electronic endoscope, reduction in diameter of the insertion portion and observation by a high-quality image are enabled by miniaturization of the image pickup device and increase in the number of pixels.

An electronic endoscope contains an image pickup unit including an expensive compact electronic component such as an image pickup device in the insertion portion. Accordingly, an electronic endoscope is generally expensive as compared with an optical endoscope in which an image guide or a relay lens is inserted through an insertion portion.

In an electronic endoscope, an endoscopic image is displayed on a screen of a display apparatus, and therefore, the advantage is provided, that observation by a plurality of users can be easily performed. In an optical endoscope, an endoscopic image can be displayed on a screen of a display apparatus by an image pickup camera (also called a camera head) including an image pickup device being fitted on an eyepiece portion.

In an electronic endoscope, the endoscope is connected to a video processor, and thereby, an optimal endoscopic image for observation is displayed on the screen of the display apparatus. In the electronic endoscope, a use state of the endoscope connected to a video processor is temporarily registered in the video processor, and thereby, an optimal endoscopic image can be obtained and observed repeatedly when the aforesaid endoscope is connected to the video processor again. Like this, an electronic endoscope has the advantage of being capable of easily displaying an endoscopic image on the display apparatus by the endoscope being connected to a video processor.

In contrast with this, in the configuration in which an image pickup camera is fitted to an eyepiece portion of an optical endoscope and an endoscopic image is displayed on the screen, the image pickup camera is attached to the eyepiece portion, and thereafter, focus has to be achieved so that the endoscopic image forms an image in a predetermined state on an image pickup surface of the image pickup camera. In other words, it may be difficult to obtain an endoscopic image optimal for observation only by attaching an image pickup camera to the eyepiece portion and connecting the image pickup camera to a video processor.

However, in the field of a rigid scope, an optical endoscope is less expensive as compared with an electronic endoscope. Accordingly, a larger number of optical rigid scopes are used as compared with electronic rigid scopes.

In the case of a laparoscopic surgical operation, the operation is generally performed with a system having a plurality of surgeons and nurses and a plurality of surgeons observe an endoscopic image displayed on a display apparatus and perform the operation. However, in an optical endoscope, in order to display an endoscopic image on the display apparatus, an image pickup camera needs to be fitted on the eyepiece portion of the endoscope as described above, while an operation of achieving focus or the like is required, and it may be sometimes difficult to obtain an optimal endoscopic image for observation easily.

Accordingly, in the field of a rigid scope for use in a laparoscopic surgical operation or the like, an electronic rigid scope capable of easily displaying a high-quality image on the screen of a display apparatus is also desired.

However, an electronic endoscope has the advantage of being capable of easily displaying a high-quality image on the display apparatus on one hand, but on the other hand, it has the disadvantage of being expensive as compared with an optical endoscope which is simple in configuration and low in component cost and assembly cost. Especially in a flexible endoscope, miniaturization of the image pickup unit is pursued for the purpose of insertability, reduction in pain of patients, and the like, and therefore, the components in use are microscopic, and much time is required in assembly, which results in a high price.

Accordingly, in an electronic endoscope, various improvements concerning reduction in cost of an image pickup apparatus have been proposed. For example, Japanese Patent Application Laid-Open Publication No. 10-216084 (hereinafter, described as Patent Document 1) shows an image pickup apparatus for an endoscope in which the image pickup apparatus at low cost can be obtained. In the image pickup apparatus for an endoscope, terminal surfaces are provided in a step shape at one circuit board, and a connecting terminal for duodenum is formed on one terminal surface in the step shape, whereas a connecting terminal for stomach is formed on the other terminal surface.

In Patent Document 1, a lead attached to a CCD is selectively connected to the connecting terminal for duodenum or stomach formed on the circuit board, whereby the attaching position of the CCD is changed, and the image pickup apparatus for duodenum and the image pickup apparatus for stomach can be obtained with one circuit board.

Further, it is conceivable to configure an image pickup unit, for example, with use of a board on which an electronic component is mounted and an image pickup device and a signal line such as a coaxial cable are connected as a common component, in a rigid scope and a flexible endoscope (or a rigid scope including a bending portion). In this case, commonality of the component can be achieved between endoscopes of different types with and without a bending portion, and therefore, the advantage of being capable of contributing to reduction in the number of process steps of management of components or the like, or cost reduction is provided, in terms of commonality between the aforesaid endoscopes of different types.

Generally in the case of an endoscope including a bending portion such as a flexible endoscope, for example, there is a demand for making the length of the rigid portion as short as possible from the viewpoint of reduction in pain at the time of insertion into the body of a patient, or enhancement in operability of the distal end portion at the time of bending. In an electronic endoscope, the size, mainly the total length of the image pickup unit which is housed in the rigid portion, exerts an influence on the length of the rigid portion.

In order to respond to the demand for making the total length of the rigid portion as short as possible, in many image pickup units for use in the endoscopes including the bending portions, connection regions for connecting the signal lines provided on the boards are usually configured to be an extremely limited spaces so that the total lengths thereof can be made short.

Since the connection regions are limited spaces, when the signal lines are connected to the boards, mechanical connection is difficult, and therefore, connection is left to manual work. More specifically, precision work is required of a worker, and the number of working process steps at the time of assembly tends to increase.

Meanwhile, for example, in the case of electronic rigid scopes without having bending portions, the demand concerning reduction in the length of the rigid portions is not high as compared with the endoscopes including bending portions. However, electronic rigid scopes tend to be expensive as compared with optical rigid scopes, and therefore, less expensive electronic rigid scopes are desired.

As described above, different demands are present between rigid scopes, and rigid scopes with bending portions including bending portions and flexible endoscopes.

SUMMARY OF THE INVENTION

An image pickup unit according to one aspect of the present invention includes: a board to which an image pickup device is electrically connected, the board being provided with a first terminal portion which includes a plurality of terminals and is used when a first endoscope is configured, and a second terminal portion which includes a plurality of terminals and is used when a second endoscope is configured; and a folding portion provided at a connection portion between the first terminal portion and the second terminal portion of the board, or a cut portion provided in a vicinity of the folding portion in the connection portion, when the board is used as an image pickup unit of the second endoscope, the board is folded at the folding portion, and the signal transmission member being connected to the second terminal portion, and at least one of a terminal size and a space between terminals in the second terminal portion being provided to be set to be larger than at least one of a terminal size and a terminal space in the first terminal portion, or when the board is used as an image pickup unit of the first endo scope, the second terminal portion being cut off at the cut portion, and the signal transmission member being connected to the first terminal portion, wherein the first endoscope is an endoscope including a bending portion in a vicinity of a distal end portion of an insertion portion in which the image pickup unit is housed, and the second endoscope is an endoscope which does not have a bending portion in a vicinity of a distal end portion of an insertion portion in which the image pickup unit is housed, with at least a vicinity of the distal end portion of the insertion portion being configured by a member which practically does not have flexibility.

An image pickup unit according to another aspect of the present invention includes an image pickup device, a board to which the image pickup device is connected, and on which an electric component is mounted; a terminal portion provided on the board, and including a plurality of terminals, to which a signal transmission member which is electrically connected to the image pickup device or the electronic component is connected, the terminal portion including a first terminal portion and a second terminal portion to which the signal transmission member is selectively connected; and a folding portion provided at a connection portion between the first terminal portion and the second terminal portion of the board, or a cut portion provided in a vicinity of the folding portion in the connection portion, when the board is used as an image pickup unit of a second endoscope, the board being folded at the folding portion, and the signal transmission member being connected to the second terminal portion, and at least one of a terminal size and a terminal space in the second terminal portion being provided to be set to be larger than a terminal size or a terminal space of the first terminal portion, or when the board is used as an image pickup unit of the first endoscope, the second terminal portion being cut off at the cut portion, and the signal transmission member being connected to the first terminal portion, wherein the first endoscope is an endoscope including a bending portion in a vicinity of a distal end portion of an insertion portion in which the image pickup unit is housed, and the second endoscope is an endoscope which does not have a bending portion in a vicinity of a distal end portion of an insertion portion in which the image pickup unit is housed, with at least a vicinity of the distal end portion of the insertion portion being configured by a member which practically does not have flexibility.

BRIEF DESCRIPTION OF THE DRAWINGS

FIG. 6 is a front view of one surface side of the board showing a wiring at a mounting surface side on which an image pickup device and an electronic component are mounted;

FIG. 7 is a transparent view of another surface side of the board explaining a wiring on the other surface side of the board from one end surface side of the board;

DETAILED DESCRIPTION OF THE PREFERRED EMBODIMENT

Hereinafter, an embodiment of the present invention will be described in detail with reference to the drawings.

One embodiment of the present invention will be described with reference to FIGS. 1 to 12.

Figure 1:
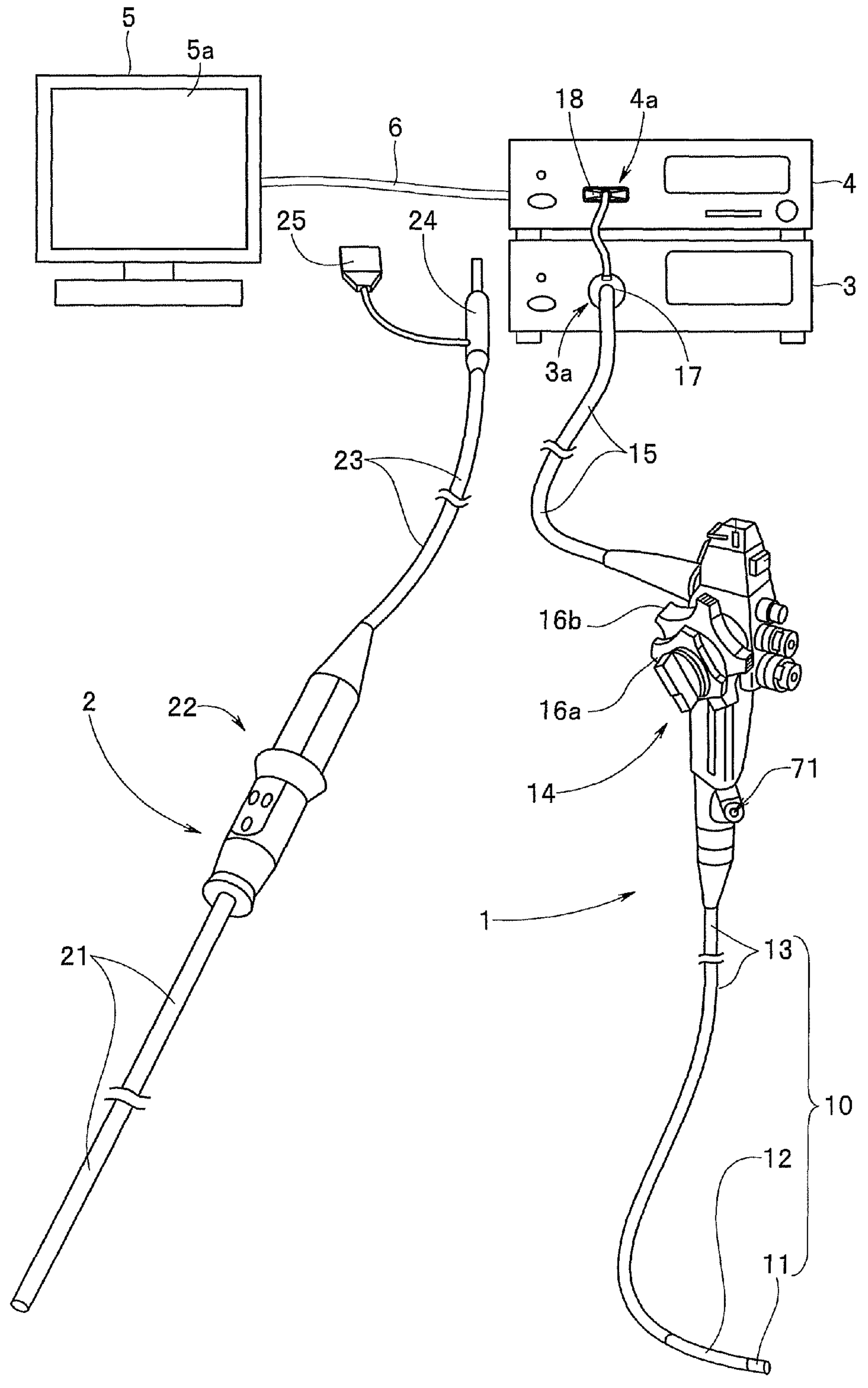
FIG. 1 is a view explaining a first endoscope and a second endoscope, and a light source apparatus, a video processor and a display apparatus which are outside apparatuses.

As shown in FIG. 1, an endoscope 1 with a bending portion (hereinafter, described as an endoscope) and a rigid endoscope (hereinafter, described as a rigid scope) 2 are respectively connected to a light source apparatus 3 and a video processor 4. An endoscopic image picked up by an image pickup device which is included by the endoscope 1 and will be described later, or an endoscopic image picked up by an image pickup device which is included by the rigid scope 2 and will be described later are displayed on a display apparatus 5.

The endoscope 1 is a first endoscope, and includes an insertion portion 10 configured by a rigid distal end portion 11, a bending portion 12 bendable in, for example, vertical and lateral directions, a flexible tube portion 13 having flexibility. An operation section 14 is connectively provided at a proximal end of the insertion portion 10. A universal cord 15 is extended from the operation section 14. The operation section 14 includes bending operation knobs 16*a* and 16*b*, which are rotatable and causes the bending portion 12 to perform a bending operation. An image pickup unit is placed in the distal end portion 11 configuring the insertion portion 10. Reference numeral 17 designates a light source connector, and reference numeral 18 designates a signal connector.

The bending directions of the bending portion 12 are set to be four directions that are upward, downward, leftward and rightward, but the bending directions may be, for example, two directions that are upward and downward. Further, the first endoscope may be a rigid scope with a bending portion including a bending portion in a vicinity of the distal end portion. In such a case, the rigid scope is configured by including a rigid tube portion instead of a flexible tube portion.

The light source apparatus 3 includes a light source connector connection portion 3*a*, and includes an illumination lamp in the apparatus. To the light source connector connection portion 3*a*, the light source connector 17, or a light source connector 24 of the rigid scope 2 is detachably connected. The video processor 4 includes a signal connector connection portion 4*a*, and includes a control unit, a signal processing circuit, a storage unit and the like in the apparatus. To the signal connector connection portion 4*a*, the signal connector 18, or a signal connector 25 of the rigid scope 2 is detachably connected. The display apparatus 5 receives a video signal outputted from the video processor 4, and displays an endoscopic image which is picked up by the endoscope 1 or the rigid scope 2 on a screen 5*a*.

The rigid scope 2 is a second endoscope, and is configured by including a rigid insertion portion 21, an operation section 22 which is connectively provided at a proximal end of the insertion portion 21, and a universal cord 23 which is extended from the operation section 22. An image pickup unit (reference numeral 30 in FIG. 2 and the like) which will be described later is placed in a distal end portion of the insertion portion 21. Reference numeral 24 designates a light source connector, and reference numeral 25 designates a signal connector.

Reference numeral 6 designates a video cable, which connects the video processor 4 and the display apparatus 5, and transmits the video signal outputted from the video processor 4.

Figure 2:
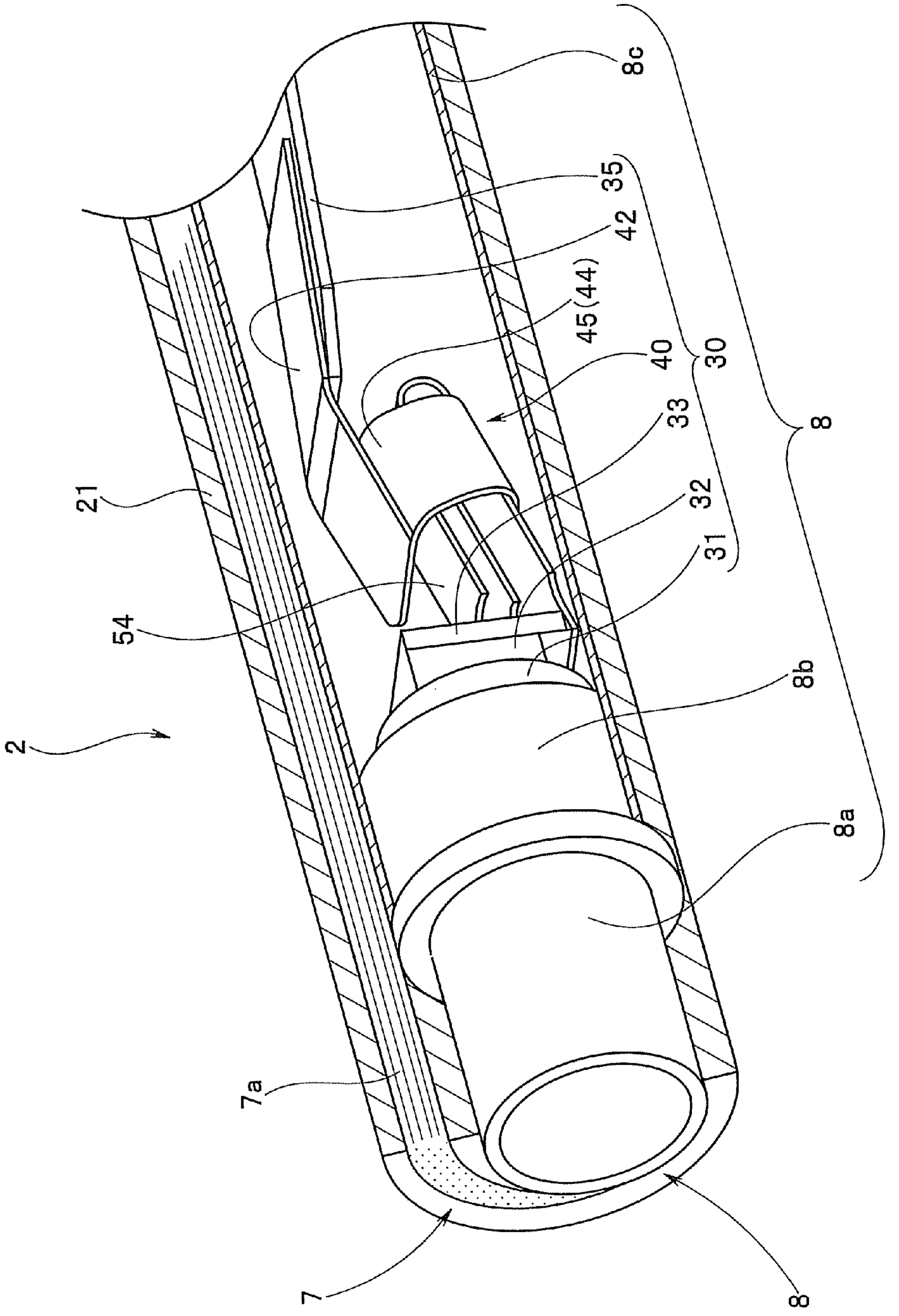
FIG. 2 is a view explaining a schematic configuration of a distal end portion of a rigid scope as the second endoscope.

As shown in FIG. 2, the rigid scope 2 includes an illumination optical system 7 and an image pickup optical system 8 in the insertion portion 21. The illumination optical system 7 is, for example, a light guide fiber bundle 7*a*, and is disposed at a predetermined position around the image pickup optical system 8. An illuminating window not illustrated is placed on a distal end face of the light guide fiber bundle 7*a*. Further, the illumination optical system is not limited to the light guide fiber bundle, but may have a configuration in which light-emitting elements such as LEDs are placed around a lens frame 8*a*.

The image pickup optical system 8 is configured by including the lens frame 8*a*, an image pickup frame 8*b*, and a rigid pipe 8*c* having a substantially circular section. Various optical lenses not illustrated are fixedly provided in the lens frame 8*a*. The image pickup frame 8*b* is fixed to the lens frame 8*a*, and a cover lens 31 which configures the image pickup unit 30 is fixed in the image pickup frame 8*b*. The rigid pipe 8*c* is fixed to the image pickup frame 8*b*, and the image pickup unit 30 is placed in the rigid pipe 8*c*.

Figure 3:
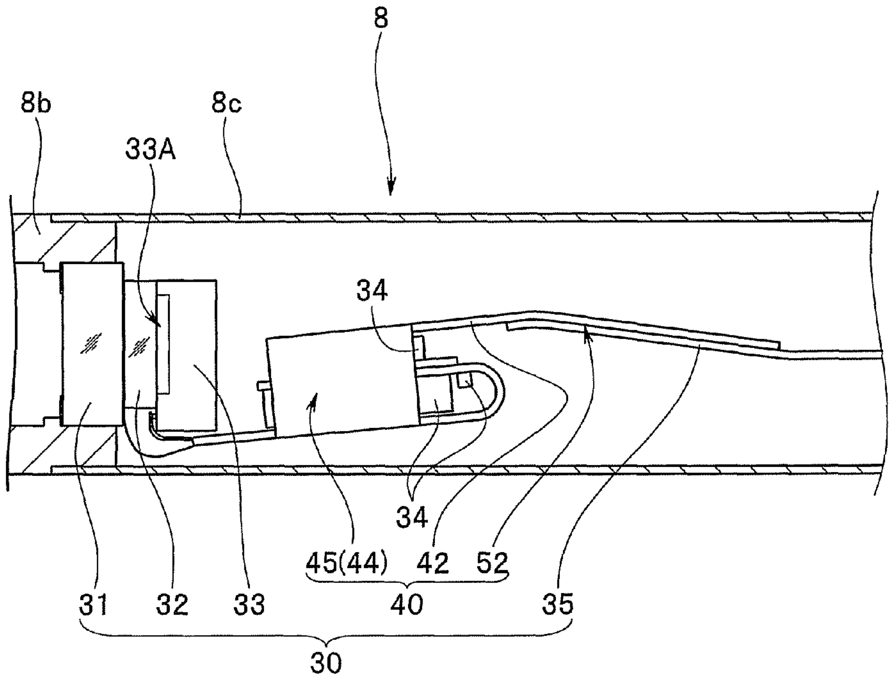
FIG. 3 is a view explaining a configuration of an image pickup unit of the rigid scope.

As shown in FIGS. 2 and 3, the image pickup unit 30 is configured by including the cover lens 31, a cover glass 32, an image pickup device 33, a board 40, and a flexible board 35 having flexibility to a thickness direction, as a signal transmission member. The image pickup device 33 is configured to be in a substantially quadrangular shape, and has a substantially quadrangular image pickup surface 33A. The cover lens 31 is formed into a circle, and has an outside diameter slightly larger than that of the image pickup surface 33A of the image pickup device 33. The cover glass 32 is formed into a substantially quadrangular shape, and has substantially the same width as the image pickup device 33. On the board 40, the image pickup device 33 and various electronic components 34 are mounted. A distal end portion of the flexible board 35 is connected to a second terminal portion 52 formed at a board portion 42 for the second endoscope which configures the board 40 and will be described later. A proximal end portion of the flexible board 35 is inserted through an inside of the rigid pipe 8*c* and is extended into the operation section 22.

The cover lens 31 and the cover glass 32 are bonded and fixed by a transparent adhesive, and the cover glass 32 is disposed on a light receiving surface of the image pickup device 33. Further, a periphery of the electronic component 34 and peripheries of electric connection portions are sealed by a nonconductive resin. A nonconductive sealing resin is charged inside the rigid pipe 8*c*.

Figure 4:
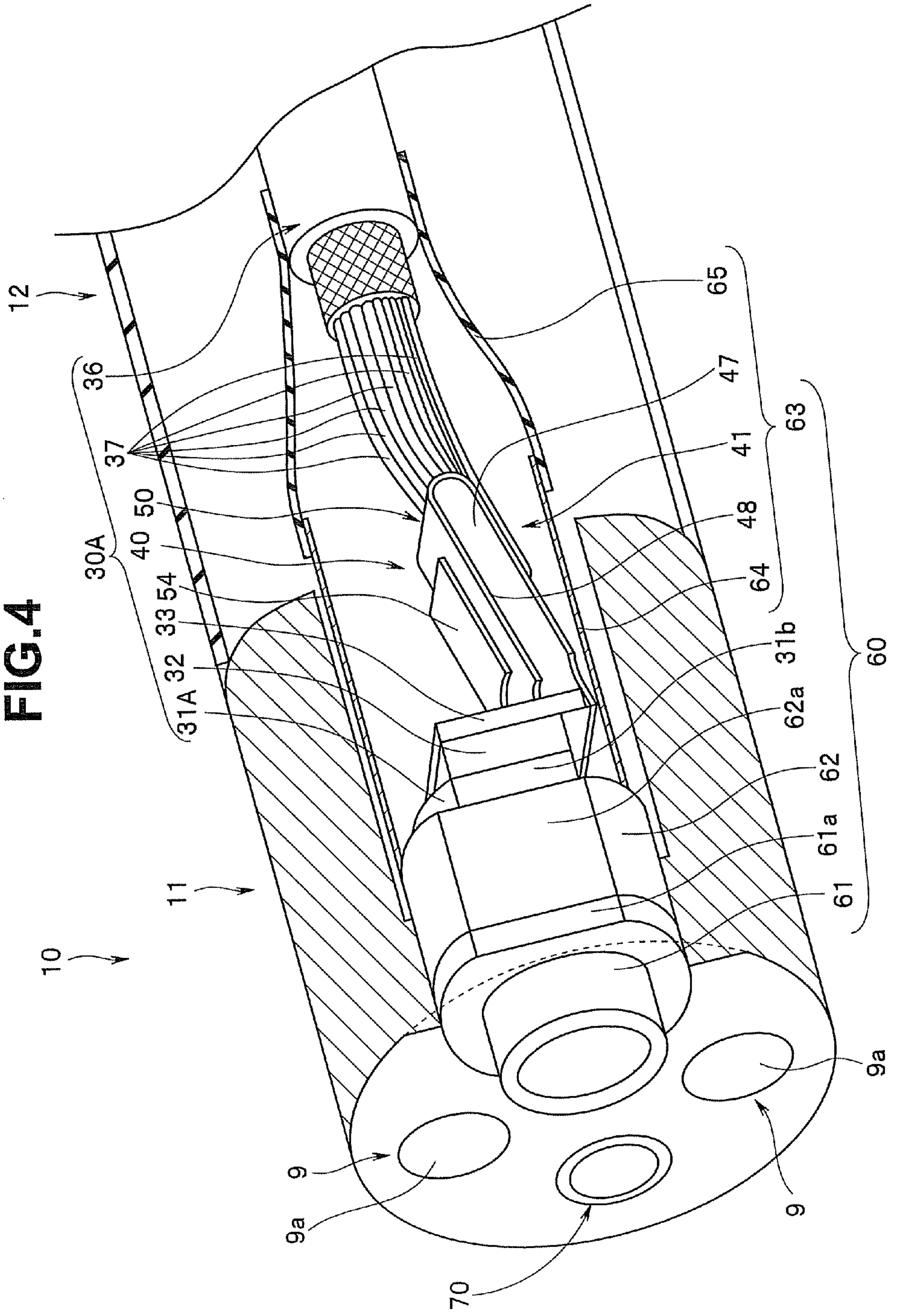
FIG. 4 is a view explaining a schematic configuration of a distal end portion of an endoscope with a bending portion as the first endoscope.

Meanwhile, as shown in FIG. 4, the endoscope 1 includes an illumination optical system 9, an observation optical system 60 and a treatment instrument channel 70 in the insertion portion 10. The treatment instrument channel 70 is mainly configured by a channel pipe sleeve (not illustrated) configured by a metal pipe, and a channel tube (not illustrated) which is connected to the channel pipe sleeve and has flexibility. The channel tube is inserted through the insertion portion 10 and is connected to a forceps insertion port 71 which is provided in the operation section 14.

A pair of illumination optical systems 9 are provided with, for example, the observation optical system 60 therebetween. The illumination optical system 9 is configured by an illuminating window 9*a* which is fixedly provided at the distal end portion 11, and a light guide fiber bundle not illustrated.

Figure 5:
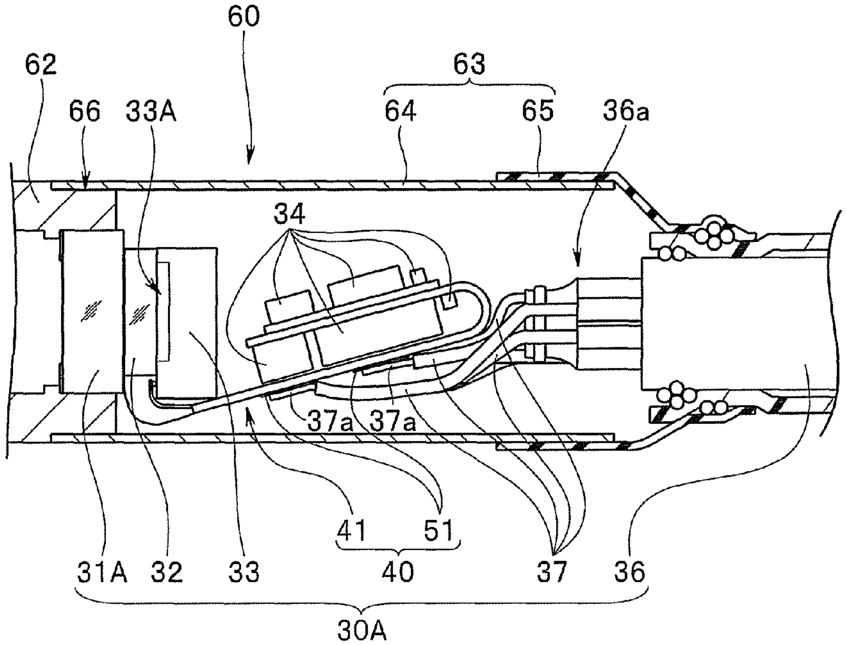
FIG. 5 is a view explaining a configuration of the endoscope with the bending portion.

As shown in FIGS. 4 and 5, the observation optical system 60 is configured by including a lens frame 61, an image pickup frame 62, and an image pickup section sheathing frame 63 configured by stacking, for example, a thin metal sheet 64 and a heat-shrinkable tube 65 in layer. The image pickup section sheathing frame 63 has its distal end portion fixed to a small-diameter portion 66 of the image pickup frame 62. On the lens frame 61 and the image pickup frame 62, at least peripheral surfaces which are disposed to be close to an outer peripheral side of the insertion portion 10, and cutout surfaces 61*a* and 62*a* configured by planes opposed to the outer periphery are formed.

A cover lens 31A configuring an image pickup unit 30A is fixed to the image pickup frame 62. The image pickup unit 30A is configured by including the cover lens 31A, the cover glass 32, the image pickup device 33, the board 40, and a signal cable 36 which is a signal transmission member. The signal cable 36 has such flexibility as to be bendable in every direction.

On the cover lens 31A of the present embodiment, at least peripheral surfaces disposed close to the outer peripheral side of the insertion portion 10, and a pair of cutout surfaces 31*b* configured by planes opposed to the outer periphery are formed.

A width of a pair of cutout surfaces of the cover lens 31A is formed to be slightly larger than a width of the image pickup device 33.

In this manner, respective pairs of cutout surfaces 61*a*, 62*a* and 31*b* are formed on the lens frame 61, the image pickup frame 62 and the cover lens 31A, and the respective cutout surfaces 61*a*, 62*a* and 31*b* are disposed substantially parallel to both side surfaces of the image pickup device 33. By such disposition, the observation optical system 60 and the treatment instrument channel 70 can be disposed to be closer to each other when the observation optical system 60 and the treatment instrument channel 70 are arranged in an axial direction orthogonal to a longitudinal direction of the insertion portion 10, and therefore, an configuration which can make an outside diameter of the distal end portion 11 smaller is provided.

The image pickup device 33 and various electronic components 34 are mounted on the board 40, and a plurality of signal lines 37 are inserted through an inside of the signal cable 36. A conductor wire portion 37*a* which each of the signal lines 37 has a sheath at a distal end side removed and exposed by a predetermined amount. The respective conductor wire portions 37*a* are respectively connected to first terminal portions (see reference numeral 51 in FIG. 7) formed on a first endoscope board portion 41 which configures the board 40 and will be described later. A proximal end portion of the signal cable 36 is inserted through an inside of the insertion portion 10, an inside of the operation section 14 and an inside of the universal cord 15 to be extended into the signal connector 18.

Figure 6:
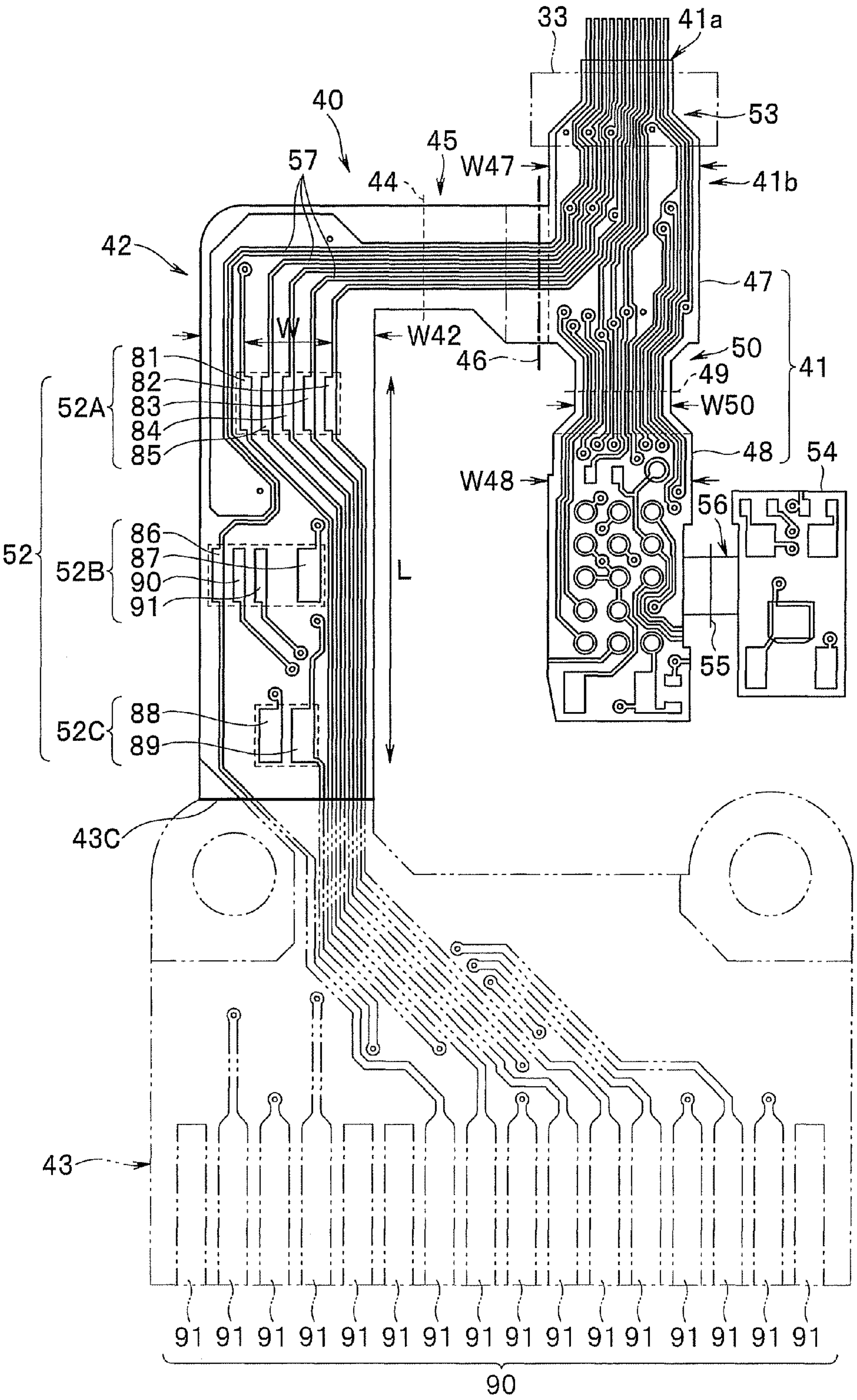
FIGS. 6 and 7 are views explaining a configuration of a board.
Figure 7:
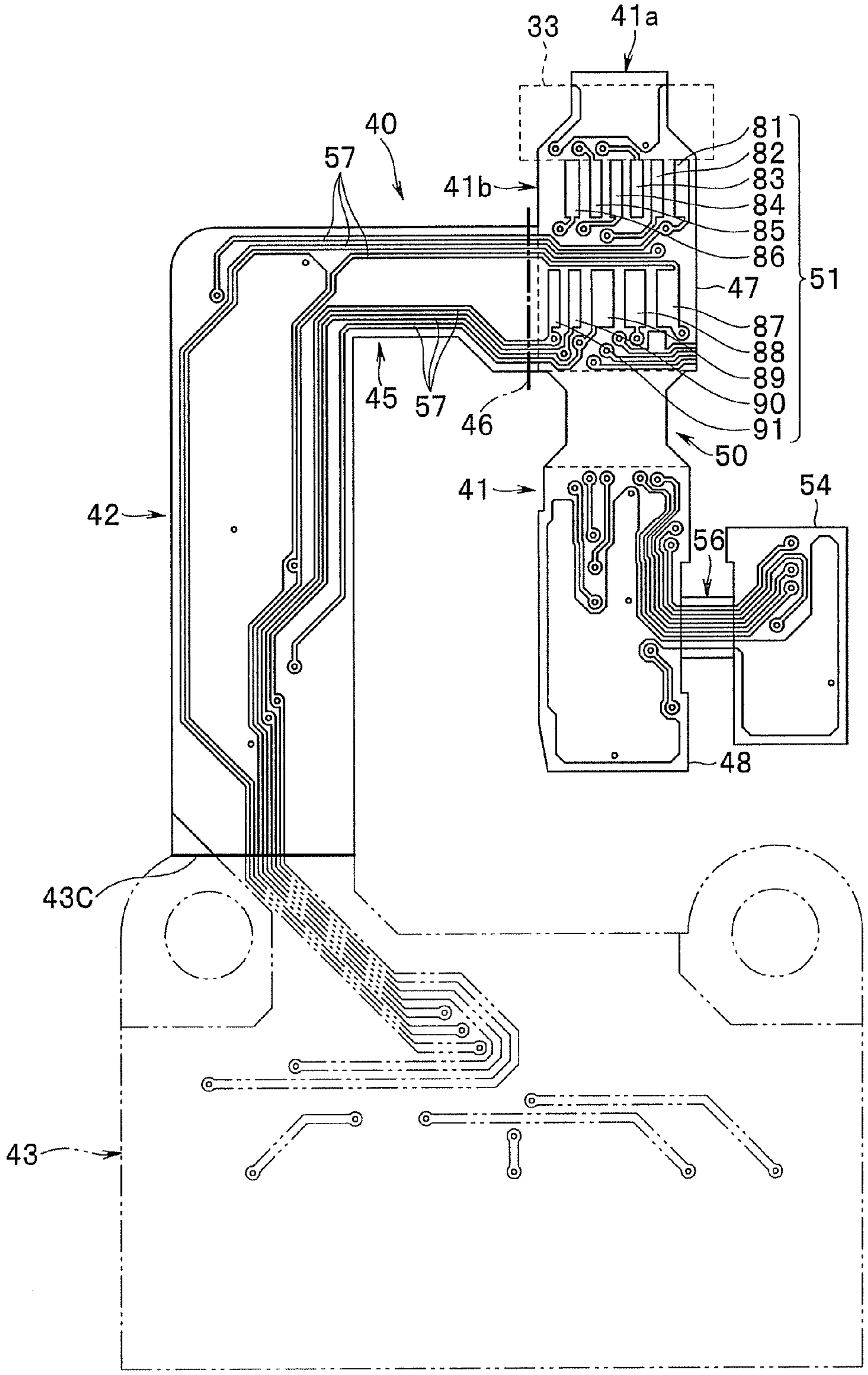

The board 40 shown in FIGS. 6 and 7 is a common board used for the image pickup unit 30A of the endoscope 1 and the image pickup unit 30 of the rigid scope 2.

The board 40 is configured by including the first endoscope board portion (hereinafter, abbreviated as a first board) 41, a second endoscope board portion (hereinafter, abbreviated as a second board) 42 and an inspection board portion 43.

The first board 41 has a substantially rectangular shape formed by a short side 41*a* substantially parallel with the image pickup device 33 and a long side 41*b* orthogonal to the short side 41*a*. The second board 42 has a substantially rectangular shape provided in parallel with the long side 41*b* of the first board 41 to be separated from the long side 41*b* by a predetermined distance. The first board 41 and the second board 42 configure the integral board 40 by a connection portion 45 including a folding portion 44 for the second endoscope shown by the broken line along which a valley fold is made.

When the second board 42 is folded to the first board 41 side along the folding portion 44 for the second endoscope, one surface side of the first board 41 and one surface side of the second board 42 are opposed to each other. Between the one surface side of the first board 41 and the one surface side of the second board 42, a gap in which the electronic component 34 mounted on the first board 41 can be disposed is configured.

The connection portion 45 has a cut portion 46 shown by the alternate long and short dashed line parallel with a side surface at the first board 41 side. When the board 40 is used as the image pickup unit 30A of the endoscope 1, the second board 42 is cut from the cut portion 46. More specifically, the aforesaid connection portion 45 has the cut portion 46 in addition to the folding portion 44 for the second endoscope.

The inspection board portion 43 is provided at a proximal end side of the second board 42. An inspection terminal portion 90 including a plurality of inspection terminals 91 is formed in the inspection board portion 43. The inspection board portion 43 is cut along a cut line 43C shown by the solid line after acceptance inspection is finished.

The first board 41 and the second board 42 respectively include terminal portions and wirings which will be described later on one surface side and the other surface side.

The first board 41 includes a first mounting portion 47 and a second mounting portion 48. A first connection portion 50 including a first folding portion 49 shown by the broken line along which a valley fold is made is provided between the first mounting portion 47 and the second mounting portion 48. The second mounting portion 48 is folded to the first mounting portion 47 side along the first folding portion 49, whereby the electronic component 34 mounted on the second mounting portion 48 is brought into a state in which the electronic component 34 is disposed over the first mounting portion 47 while facing the one surface side of the first mounting portion 47.

A width dimension W50 of the first connection portion 50 is set to be smaller than a width dimension W47 of the first mounting portion 47 and smaller than a width dimension W48 of the second mounting portion 48. According to the setting, the first connection portion 50 which is a folding portion is configured to be in a taper shape with a width dimension gradually changing to be smaller toward a proximal end side seen from a paper surface top direction of FIG. 6 when the second mounting portion 48 is brought into a folded state.

The first mounting portion 47 includes an image pickup device mounting surface 53 on which the image pickup device 33 is mounted, on one surface side, and includes a first terminal portion 51 to which the conductor wire portions 37*a* of the aforesaid signal line 37 are respectively connected, on the other surface side. The first terminal portion 51 includes, for example, terminals 81 to 91. The terminals 81 to 91 are formed by being divided into a first group in which the terminals 81 to 86 are arranged in the width direction, and a second group in which the terminals 87 to 91 are arranged in the width direction, toward the second mounting portion 48 from the image pickup device 33 side.

The one surface side of the second mounting portion 48 is the electronic component mounting surface on which the various electronic components 34 are mounted. A third mounting portion 54 on which the various electronic components 34 are mounted are provided beside the second mounting portion 48. The second mounting portion 48 and the third mounting portion 54 are integrally configured by a second connection portion 56 including a second folding portion 55 shown by the solid line along which a mounting fold is made.

When the third mounting portion 54 is folded to the second mounting portion 48 side along the second folding portion 55, the other surface side of the third mounting portion 54 is disposed over the other surface side of the second mounting portion 48. This brings about a state in which the electronic components 34 mounted on the second mounting portion 48 and the electronic components 34 mounted on the third mounting portion 54 are disposed by being stacked in layer on the first mounting portion 47.

In the present embodiment, the configuration in which the third mounting portion 54 is provided beside the second mounting portion 48 is shown, but the first mounting portion 47, the second mounting portion 48 and the third mounting portion 54 may be disposed in series, and the second folding portion 55 and the first folding portion 49 may be disposed to be in a positional relation substantially parallel with each other. Further, when the number of the electronic components 34 is small, the third mounting portion 54 is not required.

The second board 42 includes a second terminal portion 52 to which the distal end portion of the aforesaid flexible board 35 is connected, on the one surface side. A width dimension W42 of the second board 42 is set to be larger than the width dimension W47 of the first mounting portion 47 of the first board 41. This is because when the second board 42 is folded along the folding portion 44 for the second endoscope of the aforesaid connection portion 45 and is disposed over the first mounting portion 47, the second board 42 is disposed in a substantially central portion, which is wide, of the rigid pipe 8*c* as shown in FIGS. 2 to 5.

Further, since the second board 42 is the board portion which is used when the image pickup unit 30 of the rigid scope 2 is configured, the length dimension of the second board 42 is set to be an optimal length dimension in consideration of an electrical connection work of the flexible board 35.

More specifically, in the second board 42, the second terminal portion 52 is included in a region which is large in the width dimension and long in the length dimension as compared with the first mounting portion 47 including the first terminal portion 51 of the first board 41. The terminals 81 to 91 which configure the second terminal portion 52 are formed by being divided into a first group 52A in which the terminals 81 to 85 are arranged in the width direction, a second group 52B in which the terminals 86, 87, 90 and 91 are arranged in the width direction, and a third group 52C in which the terminals 88 and 89 are arranged in the width direction, from the connection portion 45 side toward the cut line 43C side. According to the configuration, spaces between the respective terminals and spaces between the respective terminal groups which are formed in the second board 42 are set to be large as compared with spaces between the respective terminals and a space between the groups formed in the first board 41. As a result, the work of connecting signal lines to the respective terminals 81 to 91 can be more easily performed in the second board 42 than in the first board 41. Accordingly, the configuration is provided, which reduces the number of assembly steps of the second endoscope, and can contribute to cost reduction.

In order to facilitate assembly, the terminal size of each of the terminals 81 to 91, namely, at least one of the terminal width and the terminal length, or the distance between the terminals, in other words, at least the spaces of the respective terminals 81 to 85 of the first group 52A in the width direction (arrow W direction in the drawing) of the second board 42 and the spaces between the respective terminals 86, 87, 90 and 91 of the second group 52B, and the distance between the first group 52A and the second group 52B in the lengthwise direction (arrow L direction in the drawing) may be set to be large.

Further, in the aforementioned embodiment, the numbers of terminals of each of the terminal portions 51 and 52 is set to be 11. However, the number of terminals is not limited to be 11, and may be not less than 11, or may be less than 11.

Figure 8:
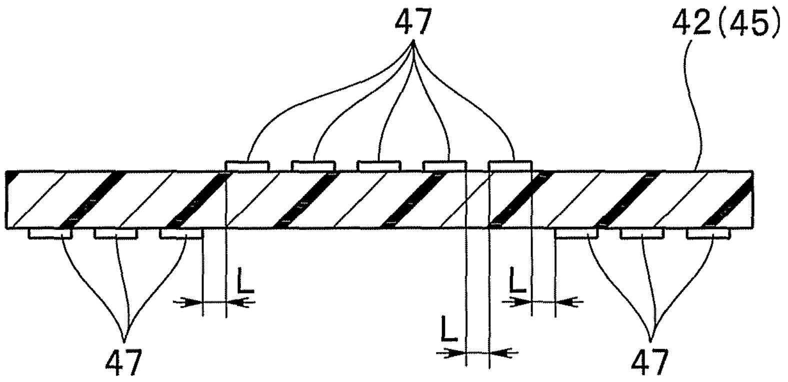
FIG. 8 is a view explaining a wiring state of wirings formed on both surfaces in a vicinity of a cut portion of a second board.

Further, wirings 57 which are extended to the second board from the first board 41 are formed on both surfaces on the one surface side and the other surface side of the connection portion 45 and the second board 42 from the cut portion 46 as shown in FIGS. 6 and 7. As shown in FIG. 8, the adjacent wirings 57 are separated from each other by a distance L so that the wiring 57 formed on the one surface side and the wiring 57 formed on the other surface side are not in the overlaid positional relation.

Here, the image pickup units 30 and 30A using the boards 40 will be described.

Figure 9:
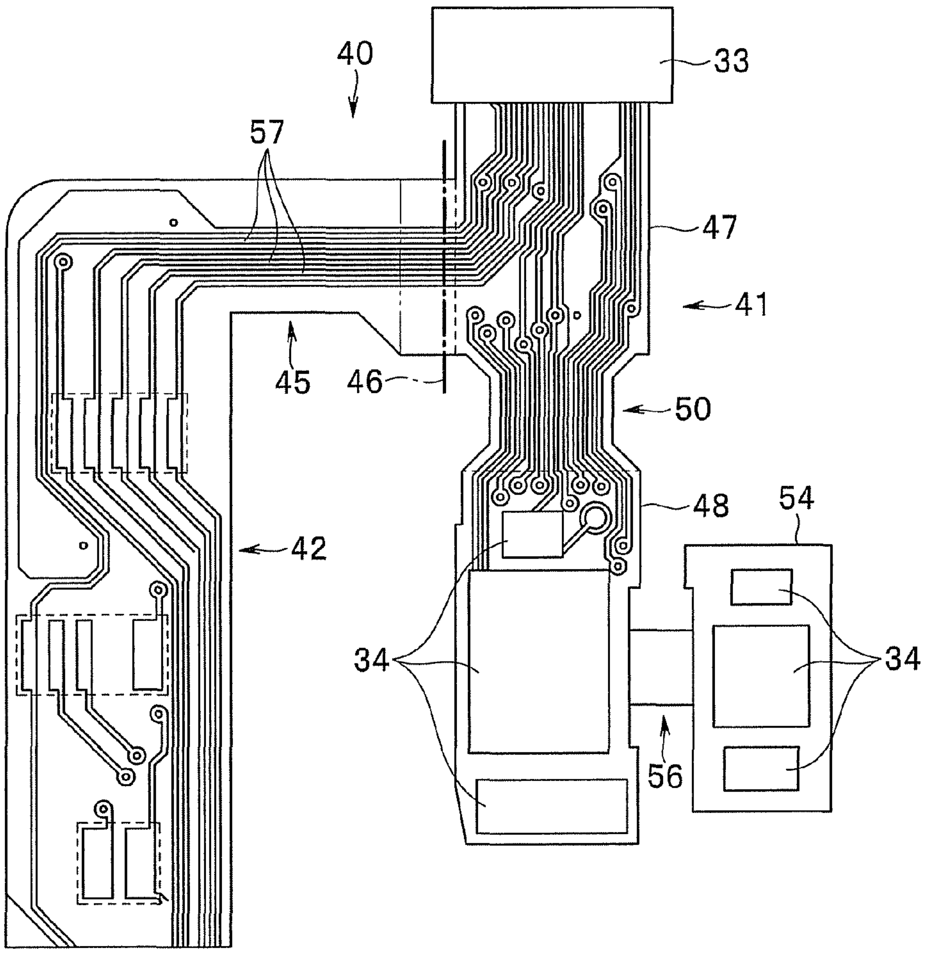
FIG. 9 is a view explaining a board which is used as an image pickup unit for the first endoscope or an image pickup unit for the second endoscope.
Figure 10:
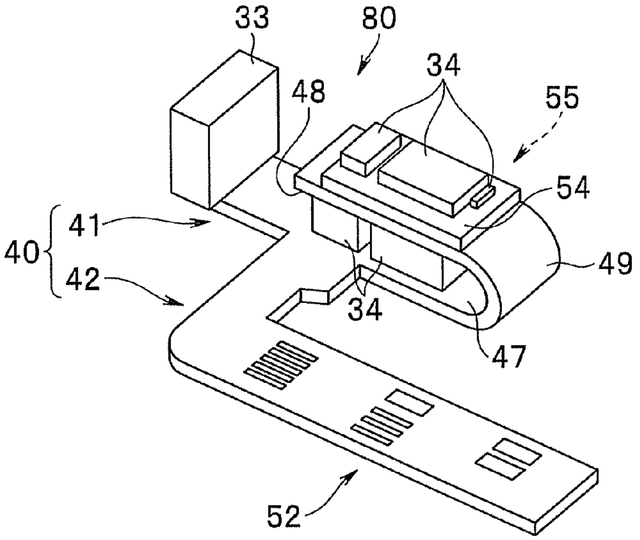
FIG. 10 is a perspective view explaining a unit portion set.

When the image pickup units 30 and 30A are configured, the image pickup device 33 and the various electronic components 34 are mounted on the board 40, and the inspection board portion 43 is cut, as shown in FIG. 9. Further, the board 40 on which the image pickup device 33 and the electronic component 34 are mounted is configured as a unit portion set 80 by being folded at the first folding portion 49 and the second folding portion 55 in predetermined states as shown in FIG. 10.

In the unit portion set 80, a plurality of electronic components 34 mounted on the second mounting portion 48, and a plurality of electronic components 34 mounted on the third mounting portion 54 are in a state stacked on the first mounting portion 47 of the first board 41. The unit portion set 80 is a common component to the image pickup units 30 and 30A.

A case of configuring the image pickup unit 30A for the endoscope 1 by using the unit portion set 80 will be described.

Figure 11:
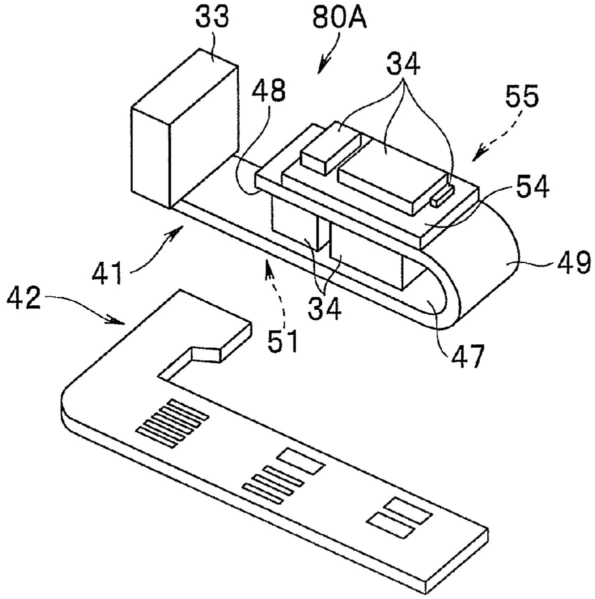
FIG. 11 is a perspective view explaining a unit portion set configuring the image pickup unit for the first endoscope.

A worker forms a unit portion set 80A for an endoscope with a bending portion by cutting the second board 42 from the cut portion 46 as shown in FIG. 11. At this time, As shown in the aforesaid FIG. 8, the wirings 57 which are respectively formed on the one surface side and the other surface side of the second board 42 are set in the positional relation in which the wirings 57 are not overlaid on each other, and thereby, cut surfaces of the wirings 57 are prevented from being in electrical contact with each other when being cut.

After the second board 42 is cut, the signal cable 36 through which a plurality of signal lines 37 are inserted is connected to the first terminal portion 51 of the unit portion set 80A for the endoscope with a bending portion. More specifically, the worker connects the conductor wire portions 37*a* of the respective signal lines 37, from which sheathing is removed, to the respective terminals 81 to 91 one by one. Subsequently, by completion of connection of the respective signal lines 37 to the respective terminals 81 to 91, the image pickup unit 30A as shown in the aforesaid FIGS. 4 and 5 is configured.

In the image pickup unit 30A, the respective terminals 81 to 91 are disposed in the vicinity of the image pickup device 33, and therefore, when the signal line 37 is connected to the first terminal portion 51, the signal line 37 is disposed on the other surface side of the first mounting portion 47 with the electronic component 34 stacked thereon. Therefore, the distal end portion 36*a* of the signal cable 36 is disposed nearer to the image pickup device 33 side, and reduction in the rigid length can be realized. Further, the cut portion 46 is provided at the first board 41 side, and thereby, the width of the image pickup unit 30A can be made small when the board is cut at the cut portion 46.

Next, the case of configuring the image pickup unit 30 for the rigid scope 2 by using the unit portion set 80 will be described.

Figure 12:
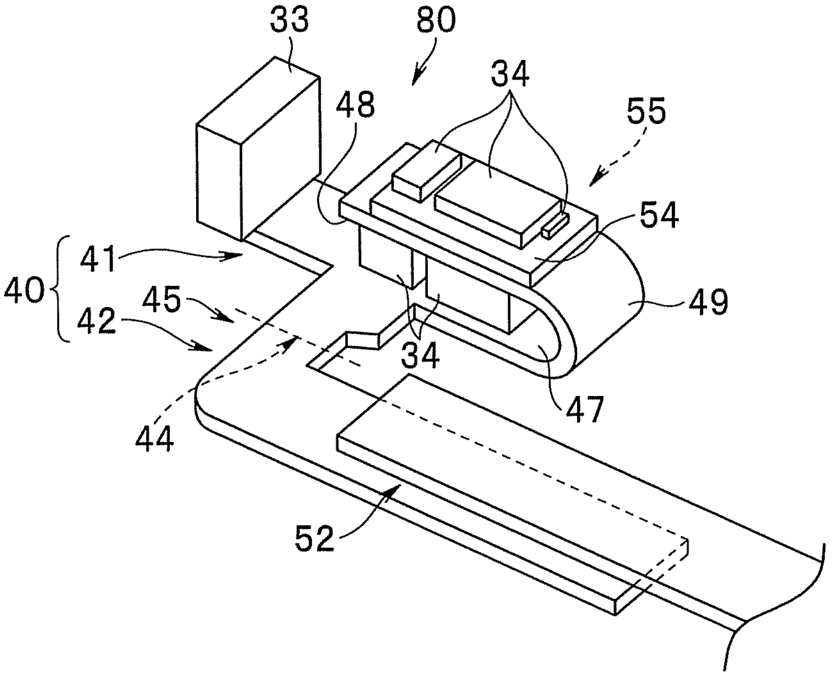
FIG. 12 is a view explaining a unit portion set and a flexible board configuring the image pickup unit for the second endoscope.

A worker connects the flexible board 35 to the second terminal portion 52 of the unit portion set 80. More specifically, the worker performs positioning by facing the flexible board 35 and the second terminal portion 52 to each other as shown in FIG. 12, and thereafter, collectively joins the flexible board 35 and the second terminal portion 52 by solder, bump, an anisotropic conductive resin or the like. Thereby, a terminal portion not illustrated of the flexible board 35 and the respective terminals 81 to 91 of the second terminal portion 52 can be electrically connected at one time.

After connecting the flexible board 35 to the second terminal portion 52 of the second board 42, the worker folds the connection portion 45 of the second board 42 along the folding portion 44 for the second endoscope. By being folded in this manner, the second board 42 to which the flexible board 35 is connected is disposed by being stacked over the first mounting portion 47 with the electronic component 34 stacked thereon, and the image pickup unit 30 as shown in the aforesaid FIGS. 2 and 3 is configured.

In the image pickup unit 30, at least one of the terminal space, the terminal group space and the terminal size of the second terminal portion 52 provided on the second board 42 is set to be larger than the terminal space, the terminal group space, or the terminal size of the first terminal portion 51 of the first board 41, and the terminal portion of the flexible board 35 is connected to the respective terminals 81 to 91 of the second terminal portion 52 instead of the signal cable 36 such as a coaxial cable having a plurality of signal lines 37 being connected thereto.

In the image pickup unit 30, the terminals 81 to 91 of the first terminal portion 51 provided on the other surface side of the first mounting portion 47 are insulated and sealed by pasting of a sealing resin or an insulating tape.

In this manner, the board 40 including the first board 41 provided with the first terminal portion 51 and the second board 42 provided with the second terminal portion 52 is configured. When the image pickup unit 30A for the endoscope having a bending portion is configured, the unit portion set 80A for the endoscope with a bending portion in which the second board 42 is cut from the board 40 is used, whereas when the image pickup unit 30 for the endoscope without a bending portion is configured, the unit portion set 80 is used without the second board 42 being cut. Thereby, the board which is made common to the image pickup units for use in the endoscope having a bending portion and the endoscope without a bending portion can be used.

The image pickup unit 30 is configured by using the unit portion set 80A for the endoscope with a bending portion, and thereby, the rigid portion length of the flexible endoscope having a bending portion can be reduced.

Further, the flexible board 35 is connected to the unit portion set 80, whereby the less expensive flexible board 35 can be inserted through the inside of the insertion portion 21 of the rigid scope 2 instead of the expensive signal cable 36 such as a coaxial cable being inserted through the inside of the insertion portion 21. Accordingly, the component of the rigid scope is made less expensive, and contribution to reduction in cost of the rigid scope can be made.

Furthermore, the spaces between the respective terminals and terminal groups formed on the second board 42 are set to be large as compared with the spaces between the respective terminals and the groups formed on the first board 41, whereby the connecting work of the terminal portion of the flexible board 35 and the respective terminals 81 to 91 can be quickly and reliably performed by positioning being performed, and therefore, reduction in the assembly cost of the rigid scope can be achieved.

Further, the work of removing sheathing of a plurality of signal lines 37 which the signal cable 36 has and exposing the conductor wire portions 37*a* by a predetermined amount is not required, whereby the working hour can be reduced, and further reduction in assembly cost can be achieved. These things can further contribute to cost reduction of the rigid scope.

The present invention is not limited only to the embodiment described above, but various modifications can be carried out within the range without departing from the gist of the present invention.

What is claimed is:

1. An image pickup unit comprising:

an image pickup device to be used with a first endoscope and a second endoscope, the first endoscope including a bending portion in a vicinity of a distal end portion of an insertion portion, the second endoscope not including a bending portion in the vicinity of the distal end portion of the insertion portion, at least the vicinity of the distal end portion of the insertion portion being configured by a member which practically does not have flexibility; and a board comprising:

a first board portion for the first endoscope provided with an image pickup device mounting surface on which the image pickup device is mounted, and with a first terminal portion on which is arranged a plurality of terminals to be respectively connected with a plurality of signal transmitting members for the first endoscope; and a second board portion for the second endoscope integrally provided to the board portion for the first endoscope with a connection portion, and provided with a second terminal portion on which is arranged a plurality of terminals to be respectively connected with a plurality of signal transmitting members for the second endoscope, wherein, when the board is used as an image pickup unit for the first endoscope, the signal transmitting members for the first endoscope are respectively connected to the terminals of the first terminal portion, and the second board portion is separated from the first board portion at a predetermined position, and wherein, when the board is used as an image pickup unit for the second endoscope, the second terminal portion is connected with the signal transmitting member for the second endoscope, and the second board portion connected with the signal transmitting member for the second endoscope is folded at a previously determined position, so that one surface of the second board portion is disposed opposite to one surface of the first board portion.

2. The image pickup unit according to claim 1, wherein the first board portion, which is provided with the first terminal portion of the board has a rectangular shape formed by a short side substantially parallel with an image pickup surface of the image pickup device to be mounted on the image pickup device mounting surface, and a long side orthogonal to the short side and the second board portion, which is provided with the second terminal portion, and is integrally provided to the first board portion with the connection portion has a rectangular shape and is provided in parallel with the long side to be separated from the long side by a predetermined distance.

3. The image pickup unit according to claim 2, wherein a width dimension of the second board portion is larger than a width dimension of a first mounting portion including the first terminal portion of the first board portion.

4. The image pickup unit according to claim 2, wherein a length dimension of the second board portion is longer than a length dimension of a first mounting portion including the first terminal portion of the first board portion.

5. The image pickup unit according to claim 2, wherein the board includes a plurality of wirings which extend to the second board portion from the first board portion through the connection portion, the wirings extending to the second board portion are formed on one surface side and another surface side of the second board portion, and the wiring formed on the one surface side in a predetermined section, and the wiring formed on the other surface side are provided in a positional relation in which the wirings are not overlaid on each other.

6. The image pickup unit according to claim 1, wherein when the board is used as the image pickup unit of the first endoscope, the signal transmission member is a signal cable which is connected to the first terminal portion, and when the board is used as the image pickup unit of the second endoscope, the signal transmission member is a flexible board which is connected to the second terminal portion.

7. The image pickup unit according to claim 1, wherein at least one of a terminal size and a space between the terminals arranged in the second terminal portion is set to be larger than a respective one of a terminal size and a space between the terminals arranged in the first terminal portion.

* * * * *